United States Patent [19]

Ozawa et al.

[11] Patent Number: 4,499,275

[45] Date of Patent: Feb. 12, 1985

[54] PHENOXYPICOLINIC ALDEHYDES

[75] Inventors: Kiyomi Ozawa; Shigeru Ishii, both of Funabashi, Japan

[73] Assignee: Nissan Chemical Industries, Ltd., Tokyo, Japan

[21] Appl. No.: 475,325

[22] Filed: Mar. 14, 1983

Related U.S. Application Data

[62] Division of Ser. No. 315,228, Oct. 26, 1981, Pat. No. 4,393,213.

[30] Foreign Application Priority Data

Jan. 14, 1981 [JP] Japan ................................. 56-3224
Jul. 6, 1981 [JP] Japan ............................. 56-105294

[51] Int. Cl.$^3$ ............................................ C07D 213/48
[52] U.S. Cl. ................................. 546/298; 546/301
[58] Field of Search ......................................... 546/298

[56] References Cited

U.S. PATENT DOCUMENTS 4,163,787 8/1979 Malhotra et al. .................. 424/263

OTHER PUBLICATIONS

Heinert et al., Tetrahedron, 1958, vol. 3, pp. 49–61.
Hetero-Aromatic Nitrogen Compounds, Pyrroles and Pyridines, 1967, p. 371, K. P. Schofield.

*Primary Examiner*—Alan L. Rotman
*Attorney, Agent, or Firm*—Frishauf, Holtz, Goodman & Woodward

[57] ABSTRACT

Novel phenoxypicolinic aldehydes, namely, 6-(4'-difluoromethoxyphenoxy)picolinic aldehyde and 5-fluoro-6-phenoxypicolinic aldehyde.

1 Claim, No Drawings

PHENOXYPICOLINIC ALDEHYDES

This is a division of application Ser. No. 315,228 filed Oct. 26, 1981 now U.S. Pat. No. 4,393,213.

The present invention relates to a novel process for producing 6-phenoxypicolinic aldehydes, and to novel picolinic aldehyde derivatives.

6-Phenoxypicolinic aldehydes are known compounds except for some, and they are useful as intermediates for the synthesis of agricultural chemicals.

For instance, they are used as staple starting materials for the production of pyrethroid insecticides which can be prepared by the following reactions.

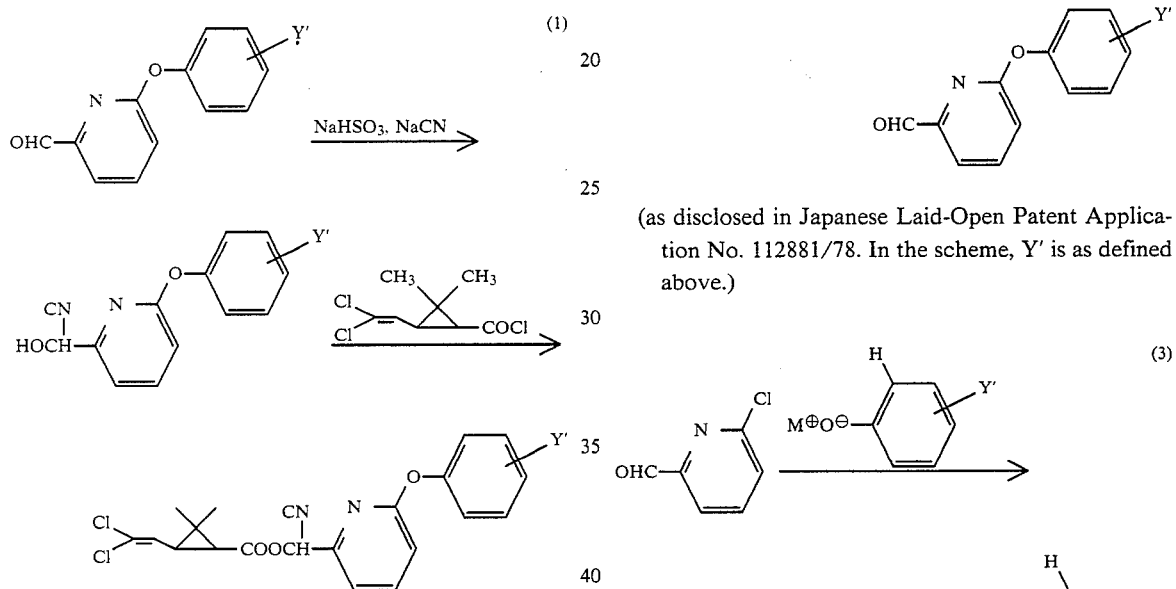

where, Y' is hydrogen, an alkyl group of 1 to 4 carbon atoms, an alkoxyl group of 1 to 4 carbon atoms, a chlorine atom, a fluorine atom, etc. (as disclosed in Japanese Laid-Open Patent Application No. 112881/78).

Cyclopropane carboxylic acid esters prepared by the above reactions are highly effective to various insect pest which are hazardous to vegetables, fruits, cotton or other plants in agriculture and horticulture as well as to insect pests such as house flies or mosquitoes in sanitation.

On the other hand, some of the picolinic aldehyde derivatives, such as 6-(4'-difluoromethoxyphenoxy) picolinic aldehyde or 5-fluoro-6-phenoxypicolinic aldehyde, are novel compounds. They can be reacted, in accordance with the above reactions (1), with a compound known as an acid component of a so-called synthetic pyrethroid, or a reactive derivative thereof, to prepare compounds having a strong insecticidal activity. Thus, they are extremely useful compounds.

Heretofore, as a method for the production of 6-phenoxypicolinic aldehydes, there has been known, for instance, a few methods represented by the following schemes:

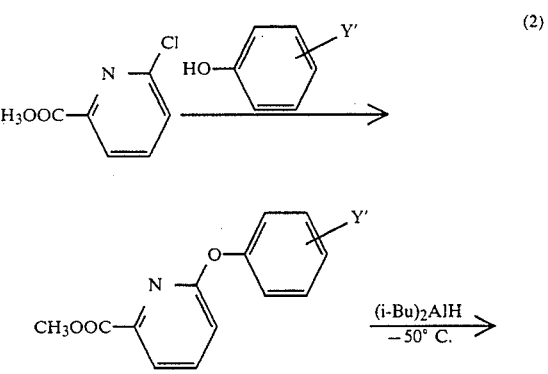

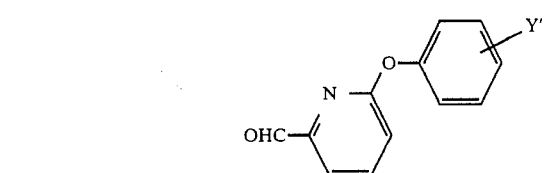

(as disclosed in Japanese Laid-Open Patent Application No. 112881/78. In the scheme, Y' is as defined above.)

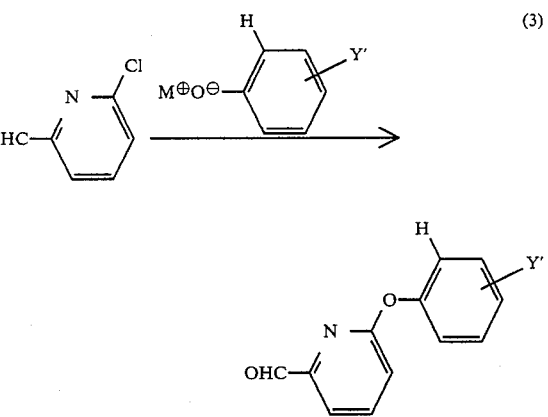

(as disclosed in U.S. Pat. No. 4,228,172. In the scheme, Y' is as defined above.)

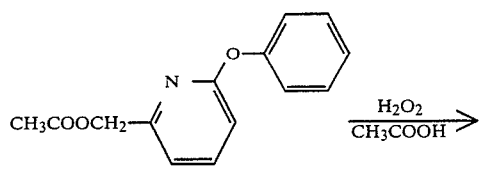

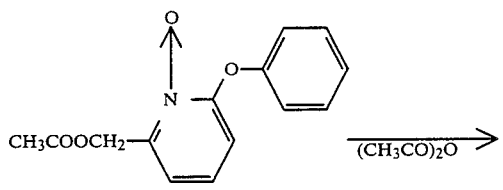

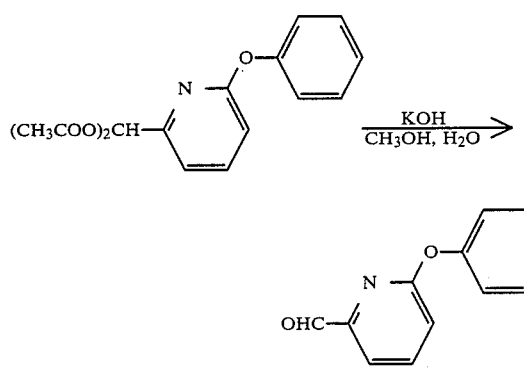

(as disclosed in U.S. Pat. No. 4,251,662).

However, the method according to the above reaction represented by the scheme (2) requires expensive reagents such as methyl 6-chloropicolinate used as a starting material for the synthesis, or diisobutyl aluminum hydride used as a reducing agent. Besides, it requires a low reaction temperature on the level of −50° C. Thus, it can not be regarded as an industrially advantageous method.

On the other hand, in the method according to the above reactions represented by the scheme (3), there is a difficulty in the industrial production of the starting material 6-halogenopicolinic aldehyde, and since the starting material is an aldehyde, a side reaction is likely to be led during the reaction with a phenol under the basic reaction condition. Therefore, there are still various problems to be solved before such a method is established as an industrial method.

On the other hand, the method according to the reaction scheme (4) can be carried out in a usual manner of operation of such reactions using inexpensive starting materials and reagents. However, it has a drawback according to many reaction steps. Further, since an aqueous hydrogen peroxide solution is used, as a reaction reagent there is a possible danger of explosion.

On the other hand, so far as the present inventors are aware, there are only the following two methods known for the synthesis of pyridine aldehydes from halogenated pyridines by means of Grignard reactions.

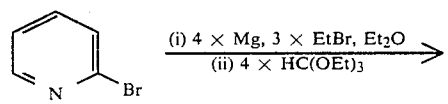 (5)

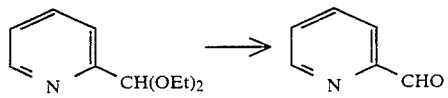

Yield: 25 to 30%

(as disclosed in Recueil des Travaux Chimiques des Pays-Bas, Vol. 71, page 1021 (1952))

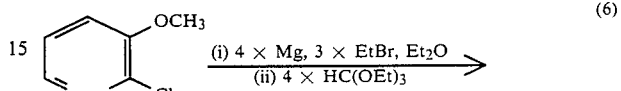 (6)

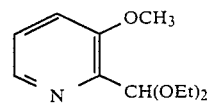

Yield: 30%

(as disclosed in Tetrahedron, Vol. 3, page 49, (1958))

However, in the reactions represented by the above reaction schemes (5) and (6), it is necessary to use ethyl bromide in an amount of 3 molar times as much as the amount of the starting material halogenated pyridine to smoothly and effectively complete the reactions. Therefore, it is necessary to use magnesium for the Grignard reaction in an amount of 4 molar times as much. Furthermore, the reagent to lead the formed Grignard reagents to the intermediates of producing aldehyde, is also required to be 4 molar times as much. Nevertheless, the yields of the aldehydes or the intermediates producing aldehyde are extremely low at a level of 20 to 30%.

Accordingly, it has been thought disadvantageous to use a Grignard reaction for the method of the production of pyridine aldehydes on an industrial scale.

The present inventors have conducted an extensive study on the production of 6-phenoxypicolinic aldehydes, and as a result, have found a novel process which is superior to the above mentioned methods, for an industrial application. Namely, it has been found possible to obtain the desired compound of high quality in good yield and in a few reaction steps by utilizing a Grignard reaction which used to be regarded disadvantageous for the production of picolinic aldehydes. Thus, the present invention has been accomplished.

The present invention relates to a process for producing 6-phenoxypicolinic aldehydes, which comprises reacting a 2-halogeno-6-phenoxypyridine represented by the general formula I

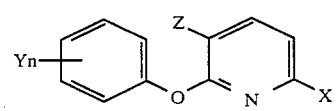 I wherein X is a halogen atom, Y is independently an alkyl group of 1 to 4 carbon atoms, an alkoxyl group of 1 to 4 carbon atoms, an alkoxyl group of 1 to 4 carbon atoms substituted by a halogen atom, an alkylthio group of 1 to 4 carbon atoms, a trifluoromethyl group, a fluorine atom or a chlorine atom. Z is a hydrogen atom or a fluorine atom, and n is an integer of 0 to 2 with magnesium metal and then with a formylating reagent, and it also relates to novel picolinic aldehydes.

Now, the process of the present invention will be described with reference to the reaction scheme (7):

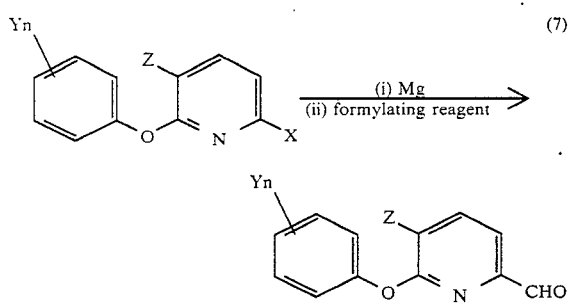

where X, Y, Z and n are as defined above.

In the reaction scheme (7), X is a halogen atom, and is preferably a chlorine atom or a bromine atom although it is not restricted to such atoms.

The starting material, 2-halogeno-6-phenoxypyridine wherein Z is a hydrogen atom, can be produced in good yield by a known method (for instance, as disclosed in French Pat. No. 1,527,714 or Rec trav. chim, Vol. 67, page 385 (1948)), for instance, by reacting 2,6-dichloropyridine or 2,6-dibromopyridine with a phenol derivative in the presence of e.g. potassium hydroxide. This starting material, for instance, 2,6-dichloropyridine, is produced on an industrial scale and is available at low costs. Likewise, 2,6-dibromopyridine is readily available.

Further, a 2-halogeno-5-fluoro-6-phenoxypyridine which is a starting material wherein Z is a fluorine atom, can be synthesized from a 2-halogeno-5-amino-6-phenoxypyridine. For instance, the desired 2-halogeno-5-fluoro-6-phenoxypyridine can be prepared by a so-called Baltz Schiemann reaction, in which the amino group at 5-position is treated with butyl nitrite together with $HPF_6$ to obtain a diazonium salt, which is then thermally decomposed.

In a case where a solvent is used in the process of the present invention, it is preferred to use a polar inert organic solvent. The polar inert organic solvent is preferably tetrahydrofuran or ethyl ether although it is not restricted to such. Tetrahydrofuran is especially preferred.

Magnesium metal may be the one which is commonly used for Grignard reactions. It is possible to use a commercially available ribbons or turnings.

The amount of the magnesium metal is preferably from 1 to 2 equivalents, more preferably from 1 to 1.2 equivalents. In certain cases, good results may be obtained by adding a reaction initiator or reaction accelerator such as iodine or ethyl bromide in order to facilitate the reaction.

However, the desired reaction will proceed even without the addition of such an additive. This is different from the conventional techniques as represented by the above reaction schemes (5) and (6). The reaction proceeds sufficiently at ambient temperature. However, in order to complete the reaction smoothly and in a short period of time, it is preferred to carry out the reaction at a temperature of 30° C. to the boiling point of the solvent. Further, as in the case of the usual Grignard reaction, it is preferred to carry out the reaction in an inert gas atmosphere.

Further, in order to carry out the reaction smoothly, it is advantageous to conduct a stirring operation. Namely, since the reaction is a reaction with magnesium metal, it is necessary to have the surface of the magnesium metal contacted always effectively with the halogenated phenoxypyridine represented by the general formula I. In most cases, it is advantageous to employ a stirring operation which is used in the reaction of this type.

In the process of the present invention, the formylating reagent is preferably a formamide such as dimethylformamide or N-methylformanilide, or an ester such as orthoformic ester or ethyl formate. Dimethylformamide is especially preferred. In the actual reaction, said formylating reagent is added to the obtained Grignard compound, normally in an amount of about 1 chemical equivalent to the Grignard compound. However, in order to avoid a vigorous reaction, it is preferred to add the reagent in small portions or to add it while cooling the reaction system at a temperature lower than room temperature. Further, for the reaction, it is also possible to replace the polar inert organic solvent (for instance, tetrahydrofuran) used for the preparation of the reaction product of a 2-halogeno-6-phenoxypyridine represented by the general formula I and magnesium metal, with other organic solvent (for instance, benzene).

Now, a specific embodiment of the process of the present invention will be given. However, the present invention is not limited to such a specific embodiment.

The starting material, a 2-halogeno-6-phenoxypyridine is dissolved in a polar inert organic solvent such as tetrahydrofuran to obtain a solution, and the solution is added to a solution which has been preliminarily prepared by adding magnesium turnings to tetrahydrofuran. In some cases, the reaction can be smoothly initiated and proceeds by preliminarily adding a minor amount of a reaction initiator such as iodine or ethylbromide.

Thereafter, a formylating reagent such as dimethylformamide is added to complete the reaction. The solvent used is then distilled off from the reaction product mixture, and then, a proper extracting solvent such as benzene or ethyl ether, and a decomposing agent such as water or diluted hydrochloric acid, are added to the residue. The separated organic layer is dried, and the organic solvent is distilled off to obtain the desired 6-phenoxypicolinic aldehyde as a crude product. The crude product is subjected to distillation or recrystallization to obtain a pure 6-phenoxypicolinic aldehyde.

Further, without subjecting the above crude product to such purification, sodium hydrogensulfite and water are added thereto, and then potassium cyanide is added to the aqueous layer, reaction mixture is extracted with ethyl ether and concentration is carried out to obtain an α-cyano-6-phenoxy-picolyl alcohol which is a derivative of the 6-phenoxypicolinic aldehyde. This compound can be used for the above mentioned synthesis of derivatives represented by the reaction formulas (1).

The merits of the process of the present invention may be enumerated as follows:

(1) The 6-phenoxypyridines halogenated at the 2-position and represented by the general formula I, as the starting material, can readily be synthesized by the reaction of 2,6-dihalogenopyridines which are industrially available at low costs, with phenols.

(2) According to the process of the present invention 6-phenoxypicolinic aldehydes can be prepared in good yield and with high quality by a Grignard reaction without requiring an additive such as ethyl bromide which is essential to the conventional method for the production of picolinic aldehydes.

(3) It is possible to produce the useful 6-phenoxypicolinic aldehydes in a few reaction steps (substantially in two steps) compared with the conventional methods.

(4) The reaction reagents used in the present invention are compounds which are industrially readily available.

Now, the process of the present invention will be described with reference to specific Examples. However, the present invention is not limited to these Examples.

REFERENCE EXAMPLE 1

Preparation of 2-halogeno-6-phenoxypyridines as the starting material

The preparation will be exemplified with respect to 2-bromo-6-(4'-chlorophenoxy)pyridine.

A mixed solution comprising 19.7 g of p-chlorophenol 23 g of potassium carbonate and 20 ml of dimethylsulfoxide, was heated at 100° C. for one hour. Then, 35.6 g of 2,6-dibromopyridine was added, and the mixture was reacted further at 100° C. for one hour. Thereafter, it was reacted at 150° C. for 8 hours. After cooling the reaction mixture, 200 ml of ethyl ether and 100 ml of water were added. After drying the organic layer over anhydrous sodium sulfate, the solvent was distilled off under reduced pressure. The residue was distilled to obtain 38.4 g having a boiling point of 144.5° C./0.7 mmHg was obtained. The distillate was crystallized when kept to stand. The melting point was 71° to 74° C.

By the nuclear magnetic resonance absorption spectra, the crystals were found to be 2-bromo-6-(4'-chlorophenoxy)pyridine.

Following this Reference Example, 2-halogeno-6-phenoxypyridines listed in the following Table 1 were prepared.

TABLE 1

| Yn | X | Boiling points °C./mm Hg | Refractive indexes or Melting points |
|---|---|---|---|
| 2-F | Cl | 113–114/0.4 | $N_D^{20}$ 1.5721 |
| 3-F | Cl | 109–110.5/0.35 | $N_D^{20}$ 1.5717 |
| 4-CH$_3$ | Cl | 124/0.33 | $N_D^{20}$ 1.5844 |
| 4-CH$_3$O | Br | 153.5–155.5/0.37 | $N_D^{20}$ 1.6079 |
| 4-CH$_3$S | Cl | 159/0.27 | m.p. 46.5–47.0° C. |
| 3-CF$_3$ | Br | 119/0.3 | $N_D^{20}$ 1.5430 |
| 3-CH$_3$, 4-Cl | Br | | m.p. 78.0–79.0° C. |

EXAMPLE 1

Into a reaction flask (5 l) equipped with a stirrer, a thermometer, a reflux condenser, a dropping funnel and a nitrogen supply tube, 29 g (1.2 gram-atom) of magnesium was introduced. Added thereto was 200 ml of dried tetrahydrofuran, and the air was substituted by nitrogen, and thereafter nitrogen was continuously supplied from the nitrogen supply tube. Dissolved in tetrahydrofuran was 250 g (1.0 mole) of 2-bromo-6-phenoxypyridine, to obtain 2 l of a solution, and a 1/10 amount (i.e. 200 ml) thereof was added into the flask.

The reaction flask was then dipped in an oil bath to maintain it at a temperature of 35° to 40° C. After the initiation of the reaction, the remaining 9/10 amount (i.e. 1800 ml) of the tetrahydrofuran solution was added dropwise while stirring in order to avoid a vigorous reaction. After the addition, the stirring was continued for further 30 minutes at 40° C. Then, the reaction flask was dipped in an ice/water bath (0° C.) to cool it, and 88 g (1.2 moles) of dimethylformamide was added dropwise in 10 minutes. Then, the reaction flask was dipped in an oil bath, and stirring was continued at 40° C. for 30 minutes. After cooling, the tetrahydrofuran was distilled off under reduced pressure, and the residue was added to 200 ml of concentrated hydrochloric acid and 2 kg of ice, thereby decomposing the remaining magnesium, and then neutralized with an aqueous solution of 1N sodium hydroxide to bring the pH to 7 to 8. The solution was transferred to a separating funnel, and 2 l of ethyl ether was added, it was adequately shaken. After washing the organic layer with a saturated aqueous sodium chloride solution and water, thr organic layer was dried over anhydrous sodium sulfate, and the ethyl ether was distilled off under reduced pressure, to obtain a crude product. This crude product was found to contain 94.6% of 6-phenoxypicolinic aldehyde by the gas chromatography (Silicone DCHV 15%/Chromosorb WAW, 60 to 80 mesh, 1 m, the temperature rise from 150° C. at a rate of 20° C./min.; Retention time: 4.3 minutes). This crude product was distilled to obtain 179 g of a compound having a boiling point of from 148.5 to 150° C./5mmHg. The yield was 89.9%. This compound was crystallized when left to stand still. The melting point was 59.5° to 61.0° C. The structure of the product was determined to be 6-phenoxypicolinic aldehyde by the nuclear magnetic resonance absorption spectra (CDCl$_3$, δ, ppm; 6.90 to 7.85 (8H, m) and 9.85 (1H, s)) and the infrared absorption spectra ($\nu$ C=O 1708 cm$^{-1}$), as well as by the elemental analysis.

| Elemental Analysis: | C (%) | H (%) | N (%) |
|---|---|---|---|
| Calculated value as C$_{12}$H$_9$NO$_2$: | 72.35 | 4.55 | 7.03 |
| Measured value: | 72.18 | 4.50 | 6.92 |

EXAMPLE 2

Into a reaction flask (5 l) equipped with a stirrer, a thermometer, a reflux condenser and a nitrogen supply tube, 48.6 g (2.0 gram-atom) of magnesium was introduced. Added thereto was 200 ml of dried tetrahydrofuran, and the system was filled with nitrogen and thereafter, nitrogen was slowly and continuously supplied. To 205.5 g (1.0 mole) of 2-chloro-6-phenoxypyridine and 109 g (1.0 mole) of ethyl bromide, tetrahydrofuran was added to bring the total amount to 2000 ml. A 1/10 amount thereof was added to initiate the reaction. After the initiation of the reaction, the reaction flask was dipped in an oil bath to keep it at a temperature of 35° to 40° C. The remaining 9/10 amount (i.e. 1,800 ml) was added dropwise while stirring to avoid a vigorous reaction. After the addition, the stirring was further continued at 40° C. for 30 minutes. Then, the reaction flask was dipped in an ice/water bath (0° C.) to cool it down, and then 146 g (2.0 moles) of dimethylformamide was added dropwise in 10 minutes. Then, the reaction flask was dipped in an oil bath and stirring was continued at 40° C. for 30 minutes. After cooling, the tetrahydrofuran was distilled off under reduced pressure, and the residue was added to 400 ml of concentrated hydrochloric acid and 4 kg of ice, thereby decomposing the remaining magnesium, and then neutralized with an aqueous solution of 1N sodium hydroxide to bring the pH to 7 to 8.

The solution was transferred to a separating funnel, and after adding 2 l of ethyl ether, it was adequately shaken. After washing the organic layer with a saturated aqueous sodium chloride solution and water, the organic layer was dried over anhydrous sodium sulfate, and concentrated under reduced pressure to obtain 199 g of a crude product. This crude product was found to contain 88.8% of 6-phenoxypicolinic aldehyde by the gas chromatography under the same condition as in Example 1.

This crude product was distilled to obtain 160 g of a product. The yield was 80.4%.

The nuclear magnetic resonance absorption spectra and the infrared absorption spectra of this product were identical with those of the product obtained in Example 1.

EXAMPLE 3

To a reaction flask (500 ml) equipped with a stirrer, a thermometer, a reflux condenser and a nitrogen supply tube, 4.9 g (0.2 gram-atom) of magnesium was introduced. Added thereto was 20 ml of dried ethyl ether, and the system was filled with nitrogen, and thereafter, nitrogen was slowly and continuously supplied.

To 25.0 g (0.10 mole) of 2-bromo-6-phenoxypyridine and 10.9 g (0.10 mole) of ethyl bromide, ethyl ether was added to bring the total amount to 200 ml. A 1/10 amount thereof was added to the reaction flask, and the reaction flask was dipped in an oil bath. The reaction was initiated while stirring under reflux. After the initiation of the reaction, the remaining 9/10 amount (i.e. 180 ml) was added dropwise while stirring to avoid a vigorous reaction. After the addition, the stirring was continued for further 30 minutes under reflux. Then, the reaction flask was dipped in a salt/ice bath ($-10°$ to $-15°$ C.) to cool it down, and then 14.8 g (0.20 mole) of ethyl formate was added dropwise to avoid a vigorous reaction. The salt/ice bath was then removed, and the stirring was continued until the temperature reaches to room temperature. The reaction mixture was added to 40 ml of concentrated hydrochloric acid and 400 g of ice, thereby decomposing the remaining magnesium, and then neutralized with an aqueous solution of 1N sodium hydroxide to bring the pH to 7 to 8. The solution was transferred to a separating funnel, and after adding 200 ml of ethyl ether, it was adequately shaken. After washing the organic layer with a saturated aqueous sodium chloride solution and water, the organic layer was dried over anhydrous sodium sulfate, and concentrated under reduced pressure to obtain 19.2 g of a crude product. The crude product was found to contain 80.1% of 6-phenoxypicolinic aldehyde by the gas chromatography under the same condition as in Example 1. This crude product was distilled to obtain 12.8 g of a product. The yield was 64.3%.

The nuclear magnetic resonance absorption spectra and the infrared absorption spectra of this product were identical with those of the product obtained in Example 1.

EXAMPLE 4

Preparation of 6-(4'-methoxyphenoxy) picolinic aldehyde

Into a reaction flask (5 l) equipped with a stirrer, a thermometer, a reflux condenser, a dropping funnel and a nitrogen supply tube, 29 g (1.2 gram-atom) of magnesium was introduced. Added thereto was 200 ml of tetrahydrofuran, and the air was substituted by nitrogen and thereafter, nitrogen was continuously supplied from the nitrogen supply tube. Dissolved in tetrahydrofuran was 280 g (1.0 mole) of 2-bromo-6-(4'-methoxyphenoxy)pyridine to obtain 2 l of a solution. A 1/10 amount (i.e. 200 ml) thereof was added to the reaction flask, and the reaction flask was then dipped in an oil bath to keep it at a temperature of 35° to 40° C. After the initiation of the reaction, the remaining 9/10 amount (i.e. 1800 ml) of the tetrahydrofuran solution was added dropwise while stirring to avoid a vigorous reaction. After the addition, the stirring was continued at 40° C. for further 30 minutes. Then, the reaction flask was dipped in an ice/water bath (0° C.) to cool it down, and then 88 g (1.2 moles) of dimethylformamide was added dropwise in 10 minutes. Then, the reaction flask was dipped in an oil bath and stirring was conitued at 40° C. for 30 minutes. After cooling, the tetrahydrofuran was distilled off under reduced pressure, and the residue was added to 200 ml of concentrated hydrochloric acid and 2 kg of ice thereby decomposing the remaining magnesium, and then neutralized with an aqueous solution of 1N sodium hydroxide to bring the pH 7 to 8. The solution was transferred to a separating funnel, and after adding 2 l of ethyl ether, it was adequately shaken. After washing the organic layer with a saturated aqueous sodium chloride solution and water, the organic layer was dried over anhydrous sodium sulfate, and ethyl ether was distilled off under reduced pressure to obtain a crude product. The crude product was found to contain 92% of 6-(4'-methoxyphenoxy)pycolinic aldehyde by the gas chromatography (Silicone DCHV 15%/Chromosorb WAW, 60 to 80 mesh, 1 m, the temperature rise from 150° C. at a rate of 20° C./min.; Retention time: 6.2 minutes).

The crude product was distilled to obtain 196 g of a compound having a boiling point of 150° to 153° C./0.19 mmHg. The yield was 85.6%. The $N_D^{23}$ was 1.5877.

The structure of the compound was confirmed by the nuclear magnetic resonance absorption spectra (CDCl$_3$, δ, ppm; 3.77 (3H, s), 6.70 to 7.98 (7H, m), 9.83 (1H, s)).

According to Example 4, compounds as shown in Table 2 were prepared.

TABLE 2

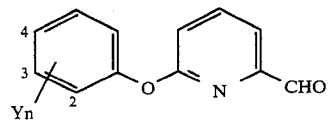

| Yn | Yield (%) | Nuclear Magnetic Resonance Absorption Spectra (CDCl$_3$, δ, ppm) | Refractive Indexes or Melting Points |
|---|---|---|---|
| 2-F | 81.0 | 7.10–8.05 (7H,m), 9.79 (1H,s) | |

TABLE 2-continued

[Structure: phenyl ring (positions 2,3,4 labeled, Yn substituent) — O — pyridine ring (N) — CHO]

| Yn | Yield (%) | Nuclear Magnetic Resonance Absorption Spectra (CDCl$_3$, δ, ppm) | Refractive Indexes or Melting Points |
|---|---|---|---|
| 3-F | 83.0 | 6.80–8.10 (7H,m), 9.85 (1H,s) | m.p. 41–43° C. |
| 4-Cl | 55.0 | 6.70–8.15 (7H,m), 9.82 (1H,s) | $N_D^{20}$ 1.5948 |
| 4-CH$_3$ | 79.0 | 2.37 (3H,s), 6.65–8.10 (7H,m), 9.84 (1H,s) | $N_D^{20}$ 1.5853 |
| 4-CH$_3$S | 84.0 | 2.47 (3H,s), 6.65–8.00 (7H,m), 9.84 (1H,s) | $N_D^{20}$ 1.6271 |
| 3-CF$_3$ | 83.0 | 7.10–8.15 (7H,m), 1.80 (1H,s) | $N_D^{20}$ 1.5312 |
| 3-CH$_3$, 4-Cl | 61.0 | 2.37 (3H,s), 6.85–8.05 (6H,m), 9.82 (1H,s) | $N_D^{20}$ 1.5987 |

EXAMPLE 5

Preparation of 6-(4'-fluorophenoxy) picolinic aldehyde

To a reaction flask (5 ) equipped with a stirrer, a thermometer, a reflux condenser, a dropping funnel and a nitrogen supply tube, 29 g of (1.2 gram-atom) of magnesium was introduced. Added thereto was 200 ml of dried tetrahydrofuran, and the air was replaced by nitrogen, and thereafter, nitrogen was continuously supplied from the nitrogen supply tube. Dissolved in tetrahydrofuran was 268 g (1.0 mole) of 2-bromo-6-(4'-fluorophenoxy)pyridine to obtain 2 l of a solution, and a 1/10 amount (i.e. 200 ml) thereof was added to the reaction flask. The reaction flask was dipped in an oil bath to bring the temperature to from 35° to 40° C. After the initiation of the reaction, the remaining 9/10 amount (i.e. 1800 ml) of the tetrahydrofuran solution was added dropwise while stirring to avoid a vigorous reaction. After the addition, the stirring was continued at 40° C. for further 30 minutes. Then, the reaction flask was immersed in an ice/water bath (0° C.) to cool it down, and then 88 g (1.2 moles) of dimethylformamide was added dropwise in 10 minutes. After cooling the tetrahydrofuran was distilled off under reduced pressure, and the residue was added to 200 ml of concentrated hydrochloric acid and 2 kg of ice, thereby decomposing the remaining magnesium, and then neutralized with an aqueous solution of 1N sodium hydroxide to bring the pH to 7 to 8. The solution was transferred to a separating funnel, and after adding 2 l of ethyl ether, it was adequately shaken. After washing the organic layer with a saturated aqueous sodium chloride solution and water, the organic layer was dried over anhydrous sodium sulfate, and the ethyl ether was distilled off under reduced pressure to obtain a crude product. This crude product was found to contain 95% of 6-(4'-fluorophenoxy)picolinic aldehyde by the gas chromatography (Silicone DCHV 15%/Chromosorb WAW, 60 to 80 mesh, 1 m, the temperature rise from 150° C. at a rate of 20° C./min.; Retention time: 4.2 minutes).

To this crude product, an aqueous solution comprising 115 g of sodium bisulfite and 2000 ml of water, was added and vigorously stirred, and then 500 ml of ethyl ether was added. The aqueous layer was taken out by a separation, and a solution comprising 150 g of sodium carbonate and 300 ml of water, was added dropwise thereto while stirring and cooling. The reaction mixture was extracted twice with 2000 ml of ethyl ether to obtain an ether layer. The ether layer was dried over anhydrous sodium sulfate, and the ethyl ether was distilled off under reduced pressure to obtain 172 g of a product. The yield was 79.3%. The $N_D^{20}$ was 1.5708.

The structure of the product was confirmed by the nuclear magnetic resonance absorption spectra (CDCl$_3$, δ, ppm; 6.70 to 8.15 (7H, m) and 9.90 (1H, s)).

EXAMPLE 6

Preparation of 6-(4'-difluoromethoxyphenoxy) picolinic aldehyde (a) Synthesis of 2-chloro-6-(4'-difluoromethoxy-phenoxy)pyridine as the starting material Added to 500 ml of dichloromethane was 23.6 g of 2-chloro-6-(4'-methoxyphenoxy)pyridine prepared in the above mentioned Reference Example 1. The mixture was cooled down to −78° C., and then 75.3 g of boron tribromide was added dropwise. After the addition, the mixture was stirred at room temperature for 24 hours, and then an aqueous potassium carbonate solution was added to bring the pH to 9. After removing the component dissolved in dichloromethane, diluted hydrochloric acid was added to the aqueous layer to neutralize it. Added thereto was 500 ml of chloroform, and extracted to obtain 20 g of 2-chloro-(4'-hydroxyphenoxy)pyridine. Then, 17.7 g of this product was added to a solution comprising 30 g of sodium hydroxide, 40 ml of water and 50 ml of dioxane, and heated at 70° to 80° C. While continuing the heating, freon 22 gas was blown in. After cooling, 150 ml of ethyl ether and 150 ml of water were added and the reaction mixture was extracted to obtain an organic layer. The organic layer was dried over anhydrous sodium sulfate, and then the ethyl ether was distilled off to obtain 18.6 g of 2-chloro-6-(4'-difluoromethoxyphenoxy)pyridine. The structure of this compound was confirmed by the nuclear magnetic resonance absorption spectra.

(b) Synthesis of 6-(4'-difluoromethoxyphenoxy)-picolinic aldehyde

The synthesis was conducted in the same manner as in Example 4. However, instead of 280 g of 2-bromo-6-(4'-methoxyphenoxy)pyridine used as the starting material in Example 4, 13.6 g of 2-chloro-6-(4'-difluoromethoxyphenoxy)pyridine obtained in the above step (a) was used, and the reaction scale was a 0.05 mole scale. Namely, the amounts of the reagents used in the reaction were 1/20 of those in Example 4. After the reaction, 12.5 g of a crude product was obtained as in the case of Example 4. This crude product was found to contain 88% of 6-(4'-difluoromethoxyphenoxy)picolinic aldehyde by the gas chromatography (Silicone DCHV 15%/Chromosorb WAW, 60 to 80 mesh, 1 m, the temperature rise from 100° C. at a rate of 10° C./min.; Retention time: 7.0 minutes). The melting point was from 40.0 to 43.0° C.

This product was purified by silica gel column chromatography (developer: benzene), and then the structure thereof was confirmed by the nuclear magnetic resonance absorption spectra (CDCl$_3$, δ, ppm; 6.55 (1H, t, J=75.0 Hz). 7.21 (4H, s), 6.90 to 8.10 (3H, m) 9.88 (1H, s)).

EXAMPLE 7

Preparation of 5-fluoro-6-phenoxypicolinic aldehyde (a) Preparation of 2-chloro-5-fluoro-6-phenoxypyridine as the starting material Dissolved in 160 ml of ethylalcohol were 45 g of 2-chloro-5-amino-6-phenoxypyridine (prepared by a known method as disclosed in West German Offenlegenschrift 2022024) and 130 g of $HPF_6$. While cooling this mixed solution at $-10°$ C., 28 g of butyl nitrite was added dropwise. After the reaction, the formed precipitate was collected by filtration, and washed with ethyl ether until the filtrate became colourless. The crystals thereby obtained were dried in vaccum at 50° C. for 8 hours to obtain 65 g of a product. This compound was transferred to a reaction flask, and gradually heated by means of a burner. Gradual decomposition with generation of a white smoke was observed. After the decomposition, an aqueous potassium carbonate solution was added for neutralization, and then 100 ml of chloroform was added for extraction to obtain a crude product.

The crude product was subjected to alumina column chromatography (developer: benzene) to remove coloured substances, and then distilled under reduced pressure to obtain 12.6 g of 2-chloro-5-fluoro-6-phenoxy-pyridine having a boiling point of 102° to 105° C./0.3 mmHg. The structure of this compound was confirmed by the nuclear magnetic resonance absorption spectra.

(b) Synthesis of 5-fluoro-6-phenoxypicolinic aldehyde

Into a reaction flask 300 ml equipped with a stirrer, a thermometer, a reflux condenser and a nitrogen supply tube, 2.43 g (0.1 gram-atom) of magnesium was introduced. Added thereto was 200 ml of dried tetrahydrofuran, and the system was filled with nitrogen and thereafter, nitrogen was slowly and continuously supplied.

To 11.2 g (0.05 mole) of 2-chloro-5-fluoro-6-phenoxypyridine and 7.1 g (0.05 mole) of methyl iodide, tetrahydrofuran was added to bring the total amount to 100 ml. A 1/10 amount thereof was added to initiate the reaction. After the initiation of the reaction, the reaction flask was dipped in an oil bath to keep it at a temperature of 35° to 40° C. The remaining 9/10 amount (i.e. 90 ml) was added dropwise while stirring to avoid a vigorous reaction. After the addition, the stirring was further continued at 40° C. for 30 minutes. Then, the reaction flask was dipped in an ice/water bath (0° C.) to cool it down, and then 7.3 g (0.1 moles) of dimethylformamide was added dropwise in 10 minutes. Then, the reaction flask was dipped in an oil bath and stirring was continued at 40° C. for 30 minutes. After cooling, the tetrahydrofuran was evaporated under reduced pressure, and the residue was added to 20 ml of concentrated hydrochloric acid and 200 g of ice, thereby decomposing the remaining magnesium, and then neutralized with an aqueous solution of 1N sodium hydroxide to bring the pH to 7 to 8.

The solution was transferred to a separating funnel, and after adding 100 ml of ethyl ether, it was adequately shaken. After washing the organic layer with a saturated aqueous sodium chloride solution and water, the organic layer was dried over anhydrous sodium sulfate, and was concentrated under reduced pressure to obtain a crude product. This crude product was found to contain 95% of the desired 5-fluoro-6-phenoxypicolinic aldehyde (retention time 4.1 minutes) by the gas chromatography (Silicone DCHV 15%/Chromosorb WAW, 60 to 80 mesh, 1 m, the temperature rise from 150° C. at a rate of 20° C./min.).

Then, this crude product was purified by silica gel column chromatography (WAKO GEL (trade name) (available from Wako Chemical Corporation) Q-23, 100 to 200 mesh, diameter of 4 cm × length of 42 cm, developer: benzene, an eluate of from 2000 ml to 2500 ml was collected), whereupon 9.3 g (86% yield) of the desired 5-fluoro-6-phenoxypicolinic aldehyde was obtained. The melting point was 66.0° to 7.10° C.

The structure of this product was confirmed by the nuclear magnetic resonance absorption spectra ($CDCl_3$, δ, ppm; 6.80 to 7.95 (7H, m), 9.64 (1H, s)) and the mass spectrography (m/z; 217 (M+) and 188 (M+-CHO)).

REFERENCE EXAMPLE 2

Synthesis of compounds having an insecticidal activity (1) Synthetis of a cyano(5-fluoro-6-phenoxy-2-pyridyl) methyl ester of α-isopropyl-p-chlorophenyl acetic acid (Compound A)

Added into 20 ml of n-hexane, were 2.2 g of 5-fluoro-6-phenoxypicolinic aldehyde prepared in Example 7, 2.3 g of α-isopropyl-p-chlorophenyl acetyl chloride, 0.6 g of sodium cyanide 1 ml of water, and 0.1 g of tetra-n-butyl ammonium chloride. This mixed solution was reacted at room temperature for 8 hours while vigorously stirring.

After the completion of the reaction, 50 ml of ethyl ether and 20 ml of water were added. The organic layer was washed with 10 ml of water, and dried over anhydrous sodium sulfate. The solvent was distilled off to obtain a crude ester. This crude product was purified by column chromatography (alumina; developer: benzene), whereupon 3.6 g of the above identified compound was obtained. The $N_D^{20}$ was 1.5464.

(2) Synthesis of a cyano(6-(4'-difluoromethoxyphenoxy)-2-pyridyl)methyl ester of α-isopropyl-p-chlorophenyl acetic acid (Compound B)

Compound B was also produced according to the above mentioned process about Compound A. However, instead of 2.2 g of 5-fluoro-6-phenoxy-picolinic aldehyde, 2.7 g of 6-(4'-difluoromethoxyphenoxy)-picolinic aldehyde prepared in Example 3 was used. The $N_D^{20}$ was 1.5365.

In an aqueous emulsion containing 100 ppm of the compounds A and B thus prepared, a leaf of Cabbage was dipped for about 10 seconds, and after drying in air, the leaf was placed in a culture dish. A secondary stage larva of tabacco cutworm was put in the culture dish, and a perforated cover was put thereon. The culture dish was placed in a constant temperature chamber for 48 hours, and mortality was determined. As the result, 100% mortality was observed with each of the compounds A and B.

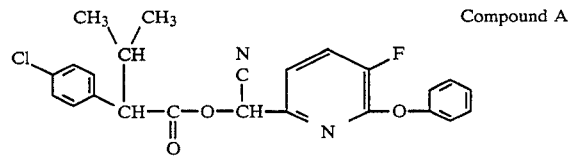

Compound A

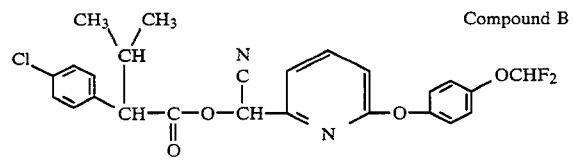

Compound B

We claim:
1. 5-Fluoro-6-phenoxypicolinic aldehyde.

* * * * *